United States Patent [19]
Molloy et al.

[11] 4,313,896
[45] Feb. 2, 1982

[54] ARYLOXYPHENYLPROPYLAMINES

[75] Inventors: Bryan B. Molloy, North Salem; Klaus K. Schmiegel, Indianapolis, both of Ind.

[73] Assignee: Eli Lilly and Company, Indianapolis, Ind.

[21] Appl. No.: 241,913

[22] Filed: Mar. 9, 1981

Related U.S. Application Data

[60] Continuation-in-part of Ser. No. 872,148, Jan. 25, 1978, which is a division of Ser. No. 432,379, Jan. 10, 1974.

[51] Int. Cl.$^3$ .............................................. C07C 93/06
[52] U.S. Cl. ............................ 260/501.18; 424/316; 424/330; 564/347
[58] Field of Search .................... 260/501.18; 564/347

[56] References Cited

U.S. PATENT DOCUMENTS

| | | | |
|---|---|---|---|
| 2,683,742 | 7/1954 | Cusic | 564/346 X |
| 3,106,564 | 10/1963 | Fleming et al. | 564/347 X |
| 3,132,179 | 5/1964 | Clark | 564/347 X |
| 3,253,040 | 5/1966 | Potter et al. | 564/347 X |
| 3,562,330 | 3/1971 | Nordin | 564/355 |

OTHER PUBLICATIONS

Wong et al., J. Pharm. & Exper. Therap., 193, 801 (1975).
Fuller et al., Biochem. Pharm. 27, 193 (1977).
Lemberger et al., Clin. Pharmacol. Ther., 23, 421 (1978).
J. Pharm. Soc. (Japan) 93, 508, 1144, 1154 (1973).

Primary Examiner—Robert V. Hines
Attorney, Agent, or Firm—James L. Rowe; Arthur R. Whale

[57] ABSTRACT

3-Aryloxy-3-phenylpropylamines and acid addition salts thereof, useful as psychotropic agents, particularly as anti-depressants.

4 Claims, No Drawings

ARYLOXYPHENYLPROPYLAMINES

CROSS-REFERENCE

This application is a continuation-in-part of our copending application Ser. No. 872,148 filed Jan. 25, 1978 which is a division of our copending application Ser. No. 432,379 filed Jan. 10, 1974.

BACKGROUND OF THE INVENTION

Tertiary 2-phenoxy-2-phenylethylamines constitute the subject matter of U.S. Pat. No. 3,106,564. The compounds are said to be useful pharmacological agents exhibiting activity on the central nervous system including useful application as analeptic agents without significant effect on respiration. The compounds are also said to have a high order of activity as antihistaminic and anticholinergic agents. Several tertiary 3-phenoxy-3-phenylpropylamines, 3-phenoxy-3-phenylpropylamine itself and some corresponding quaternary ammonium compounds are disclosed in *J. Pharmaceutical Society, Japan,* 93, 508–519, 1144–53, 1154–61 (1973). The compounds are said to be mydriatic agents.

Two U.S. Pat. Nos. 4,018,895 and 4,194,009, based on divisional applications identical in disclosure to Ser. No. 432,379, have issued.

SUMMARY OF THE INVENTION

This invention provides 3-aryloxy-3-phenylpropylamines of the formula:

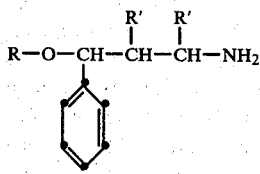

wherein each R' is independently hydrogen or methyl; wherein R is naphthyl or

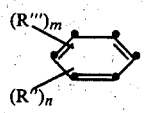

wherein R" and R''' are halo, trifluoromethyl, $C_1$-$C_4$ alkyl, $C_1$-$C_3$ alkoxy or $C_3$-$C_4$ alkenyl; and wherein n and m are 0, 1 or 2; and acid addition salts thereof formed with pharmaceutically-acceptable acids.

In the above formula when R is naphthyl, it can be either α-naphthyl of β-naphthyl. R" and R''' when they are halo, $C_1$-$C_4$ alkyl, $C_1$-$C_3$ alkoxy or $C_3$-$C_4$ alkenyl represent, illustratively, the following atoms or groups: fluoro, chloro, bromo, iodo, methyl, ethyl, isopropyl, n-propyl, n-butyl, isobutyl, sec.-butyl, t-butyl, methoxy, ethoxy, n-propoxy, isopropoxy, allyl, methallyl, crotyl and the like. R thus can represent o, m and p-trifluoromethylphenyl, o,m and p-chlorophenyl, o,m and p-bromophenyl, o,m and p-fluorophenyl, o,m and p-tolyl, xylyl including all position isomers, o,m and p-anisyl, o,m and p-allylphenyl, o,m and p-methylallylphenyl, o,m and p-phenetolyl(ethoxyphenyl), 2,4-dichlorophenyl, 3,5-difluorophenyl, 2-methoxy-4-chlorophenyl, 2-methyl-4-chlorophenyl, 2-ethyl-4-bromophenyl, 2,4,6-trimethylphenyl, 2-fluoro-4-trifluoromethylphenyl, 2,4,6-trichlorophenyl, 2,4,5-trichlorophenyl, and the like. Compounds illustrative of the scope of this invention include the following:

3-(p-isopropoxyphenoxy)-3-phenylpropylamine methanesulfonate 3-(2'-methyl-4',5'-dichlorophenoxy)-3-phenylpropylamine nitrate 3-(p-t-butylphenoxy)-3-phenylpropylamine glutarate 3-(2'-chloro-p-tolyloxy)-3-phenyl-1-methylpropylamine lactate 3-(2',4'-dichlorophenoxy)-3-phenyl-2-methylpropylamine citrate 3-(m-anisyloxy)-3-phenyl-1-methylpropylamine maleate 3-(p-tolyloxy)-3-phenylpropylamine sulfate 3-(2',4'-difluorophenoxy)-3-phenylpropylamine 2,4-dinitrobenzoate 3-(o-ethylphenoxy)-3-phenylpropylamine dihydrogen phosphate 3-(2'-chloro-4'-isopropylphenoxy)-3-phenyl-2-methylpropylamine maleate 3-(2'-allyl-4'-fluorophenoxy)-3-phenylpropylamine succinate 3-(o-isopropoxyphenoxy)-3-phenylpropylamine phenylacetate 3-(o-bromophenoxy)-3-phenylpropylamine-β-phenylpropionate 3-(p-iodophenoxy)-3-phenylpropylamine propiolate 3-(3' or n-propylphenoxy)-3-phenylpropylamine decanoate Also included within the scope of this invention are the pharmaceutically-acceptable salts of the amine bases represented by the above formula formed with nontoxic acids. These acid addition salts include salts derived from inorganic acids such as: hydrochloric acid, nitric acid, phosphoric acid, sulfuric acid, hydrobromic acid, hydriodic acid, phosphorous acid and the like, as well as salts of nontoxic organic acids including aliphatic mono and dicarboxylates, phenyl-substituted alkanoates, hydroxy alkanoates and alkanedioates, aromatic acids, aliphatic and aromatic sulfonic acids etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonates, naphthalene-1-sulfonate, naphthalene-2-sulfonate, mandelate and the like salts.

The compounds of this invention in the form of their free bases are high boiling oils, but white crystalline solids in the form of their acid addition salts. The compounds can be prepared in several ways. A particularly useful procedure for preparing compounds represented by the above formula is carried out as follows:

3-Chloropropylbenzene is reacted with a positive halogenating agent such as N-bromosuccinimide to yield the corresponding 3-chloro-1-bromopropylbenzene. Selective replacement of the bromine atom with the sodium salt of a phenol, as for example, the sodium salt of o-methoxyphenol (guiacol) yields a 3-chloro-1-(o-methoxyphenoxy)propylbenzene [also named as 3-chloro-1-(o-anisyloxy)propylbenzene]. Reaction of the 3-chloro derivative thus produced with sodium azide yields the corresponding 3-azido-1-(o-anisyloxy)propylbenzene. Reduction of the azide group with a metalloorganic reducing agent such as sodium borohydride yields the desired primary amine. Alternatively, the chloro compound can be reacted directly with a large excess of ammonia in a high pressure reactor to give the primary amine.

The compounds of this invention can also be prepared by debenzylation of the corresponding N,N-dibenzyl tertiary amines or N-benzyl secondary amine. A useful preparation of an N,N-dibenzyl tertiary amine follows:

β-Dibenzylaminopropiophenone produced by a Mannich reaction is reduced to yield N,N-dibenzyl 3-phenyl-3-hydroxypropylamine. Replacement of the hydroxyl group with a halogen, such as chlorine, yields the corresponding N,N-dibenzyl 3-phenyl-3-chloropropylamine. Reaction of this chloro compound with a saltably substituted phenol, as for example o-methoxyphenol (guiacol), produces N,N-dibenzyl 3-phenyl-3-(o-anisyloxypropylamine. Hydrogenation of this N,N-dibenzyl compound in the presence of Raney nickel or other suitable catalyst serves to remove both benzyl groups to produce the corresponding primary amine.

A secondary N-benzylamine can likewise be debenzylated to produce the desired primary amine. To prepare such a secondary benzlamine, 3-chloro-1-(o-anisyloxy)propylbenzene or other 1-substituted phenyl-3-chloropropylbenzene, utilized as an intermediate in an earlier procedure, can be reacted with benzylamine to yield N-benzyl 3-phenyl-3-(o-anisyloxy)propylamine.

Compounds in which the R' group on the carbon atom alpha to the nitrogen is methyl can be prepared by reacting phenyl 2-propenyl ketone with dibenzylamine [See method of *J. Am. Chem. Soc.,* 75, 4460 (1953)]. The resulting 3-dibenzylaminobutyrophenone is reduced to yield the N,N-dibenzyl 3-hydroxy-1-methyl-3-phenylpropylamine. Replacement of the hydroxyl with chlorine followed by reaction of the chloro-compound with the sodium salt of a suitably substituted phenol yields an N,N-dibenzyl derivative bearing an alpha methyl group on the propylamine backbone of the molecule. Production of the corresponding primary amine can be accomplished by the aforementioned catalytic debenzylation procedure.

Compounds in which the R' group attached to the β-carbon atom is methyl are prepared by a Mannich reaction involving propiophenone, formaldehyde and dibenzylamine. The resulting ketone, an α-methyl-β-dibenzylaminopropiophenone, is subjected to the same reduction procedure as before to yield a hydroxy compound. Replacement of the hydroxyl with chlorine followed by reaction of the chloro compound with the sodium salt of a phenol yields a dibenzyl amine derivative. Conversion of the dibenzylamine to the corresponding primary amines is carried out as before.

Those compounds in which the R' group attached to either the α or β-carbon is methyl have two asymmetric carbon atoms, the carbon carrying the R' methyl and the γ-carbon carrying the phenoxy and phenyl groups. Thus, such compounds exist in two diastereomeric forms occurring as two racemic pairs, the less soluble pair being designated α-dl form and the more soluble the β-dl form. Where each R' is hydrogen, there is only one asymmetric center, the γ-carbon carrying the phenyl and phenoxy groups. Each racemate can be resolved into its individual d and l isomers by methods well known in the art, as by forming salts with optically active acids and separating the salts by crystallization.

This invention is further illustrated by the following specific examples:

EXAMPLE 1

Preparation of 3-(o-methoxyphenoxy)-3-phenylpropylamine

A solution of 2.6 g. of sodium azide in 10 ml. of water was placed in a 100 ml. three-neck, round-bottom flask equipped with stirrer, condenser and thermometer. A second solution containing 2.76 g. of 3-chloro-1-(o-methoxyphenoxy)propylbenzene in 30 ml. of dimethylformamide was added to the sodium azide solution, and the resulting mixture heated at 95° C. overnight. The reaction mixture was cooled, diluted with water and extracted three times with ether. The ether extracts were combined, the combined extracts were washed five times with water followed by a saturated aqueous sodium chloride wash, and were then dried. Evaporation of the ether in vacuo yielded a colorless liquid comprising 3-azido-1-(o-methoxyphenoxy)propylbenzene. Forty-one grams of this latter compound were dissolved in 350 ml. of isopropanol. The resulting solution was placed in a 1 l. round-bottom flask equipped with magnetic stirrer condenser and drying tube. Fifteen and two-tenths grams of 96% sodium borohydride in the solid form were added to the azide solution. The resulting mixture was heated at reflux temperature overnight and then cooled. The alcohol was evaporated therefrom in vacuo. About 1.5 l. of water were added, and the resulting aqueous mixture acidified cautiously with 2 N aqueous hydrochloric acid. 3-(o-methoxyphenoxy)-3-phenylpropylamine produced in the above reaction was soluble in the aqueous acidic layer as the hydrochloride salt. The acidic aqueous layer was extracted three times with ether, and the ether extracts saved to recover unreacted starting material. The acidic layer was then made basic with 5 N aqueous sodium hydroxide. The primary amine, being insoluble in base, separated and was extracted into ether. The ether layer was separated, and the aqueous alkaline layer extracted twice more with ether. The ether extracts were combined, and the combined extracts were washed with a saturated aqueous sodium chloride solution and then dried. Evaporation of the ether in vacuo yielded about 17 g. of 3-(o-methoxyphenoxy)-3-phenylpropylamine which was converted to the oxalate salt by dissolving the compound in ether and adding a solution of oxalic acid in ether thereto. 3-(o-Methoxyphenoxy)-3-phenylpropylamine oxalate thus prepared melted at 118°–121° C. after recrystallization from an ethyl acetate-methanol solvent mixture. The oxalate salt was converted to the hydrochloride salt by forming the free base in ether solution and then saturating the ether solution with gaseous hydrogen chloride. The hydrochloride salt melted at 77°–80° C. Analysis; Calc.: C, 65.41; H, 6.86; N, 4.77; Cl, 12.07; Found: C, 65.13; H, 7.12; N, 4.61; Cl, 12.21.

EXAMPLE 2

Preparation of 3-phenoxy-3-phenylpropylamine

A reaction mixture consisting of 1000 g. of 3-chloropropylbenzene, 1500 g. of N-bromosuccinimide, 5 g. of benzoyl peroxide and 6 l. of carbon tetrachloride were placed in a 12 l. 3-neck, round-bottom flask equipped with stirrer and condenser. The reaction mixture was stirred and heated until an exothermic reaction began. The heat source was then removed, after the exothermic reaction had subsided, the reaction mixture was refluxed until the reaction was completed as noted by the disappearance of the N-bromosuccinimide. The reaction mixture was then cooled and crystalline succinimide collected by filtration. The succinimide filter cake was washed with carbon tetrachloride. The combined filtrate and wash was concentrated in vacuo. The residue comprising 3-chloro-1-bromopropylbenzene obtained in the above reaction, was shown by a NMR to be the desired material and was used without further purification. The yield was essentially quantitative.

Next, a solution of sodium phenolate was prepared by dissolving 40 g. of sodium hydroxide in 900 ml. of ethanol. 94.1 g. of phenol were added to the solution maintained at room temperature. The ethanol was removed by evaporation in vacuo, benzene added, and the benzene also removed by evaporation in vacuo. This process was repeated several times in order to dry completely the sodium phenolate formed in the above reaction.

The sodium phenolate obtained by the above procedure was suspended in approximately 1000 ml. of dimethylsulfoxide. The solution was cooled to about 20° C. About 1 mole of 3-chloro-1-bromopropylbenzene was added thereto in dropwise fashion over a period of ¼ hour while the reaction temperature was maintained at about 25° C. The reaction mixture was allowed to stir at room temperature overnight and was then poured onto 3 l. of an ice-water mixture and extracted three times with n-hexane. The hexane extracts were washed with water and dried. Removal of the hexane in vacuo yielded as a residue comprising 3-phenoxy-3-phenylpropylchloride; the compound distilled in vacuo in the range 143°-146° C. (1.0-1.1); yield=102.4 g. The structure of the compound was verified by NMR.

Eight grams of 3-phenoxy-3-phenylpropylchloride were heated with 150 ml. of liquid ammonia in a high pressure reactor at 100° C. for 20 hours. The volatile constituents of the reaction mixture were evaporated, and the residue, comprising 3-phenoxy-3-phenylpropylamine formed in the above reaction, was dissolved in ethanol and the volatile constituents again removed by evaporation. The resulting residue was dissolved in a mixture of ether and 5 N aqueous sodium hydroxide. The ether layer was separated, and the alkaline aqueous layer extracted three more times with ether. The ether extracts were combined, and the combined extracts washed with water. The combined ether extracts were in turn extracted twice with 2 N aqueous hydrochloric acid, the primary amine passing into the acidic layer. The acidic extracts were combined and made basic by the addition of an excess of 5 N aqueous sodium hydroxide. The primary amine, being insoluble in the basic layer, separated and was extracted into ether. The ether extract was separated, and the basic solution extracted twice more with ether. The ether extracts were combined, the combined extracts washed with saturated aqueous sodium chloride and then dried.

Evaporation of the ether in vacuo yielded 3-phenoxy-3-phenylpropylamine as an oil. The oxalate salt of the primary amine was prepared and melted at 170°-173° C.

Analysis: Calculated: C, 64.34; H, 6.04; N, 4.41; Found: C, 64.49; H, 5.80; N, 4.67.

EXAMPLE 3

Preparation of 3-phenyl-3-(p-trifluoromethylphenoxy)propylamine

One kilogram of 3-chloropropylbenzene was dissolved in 1.5 gallons of carbon tetrachloride in a 22 l. flask. 1193 g. of N-bromosuccinimide were added followed by 5 g. of benzoylperoxide. The reaction mixture was heated to refluxing temperatures for about five hours, and was then cooled. A white solid which separated was isolated by filtration. The white solid was washed with cold carbon tetrachloride. The solvent was removed from the filtrate by evaporation in vacuo yielding 1538 g. of 3-chloro-1-bromopropylbenzene.

A solution was prepared by dissolving 485 g. of p-trifluoromethylphenol in about 2.5 l. of ethanol. 146 g. of sodium hydride as a 50 percent suspension in mineral oil was added, thus forming the sodium salt of the phenol. The sodium salt was dried by evaporation in vacuo using a benzene azeotrope. The dried sodium salt of p-trifluoromethylphenol was dissolved in 1.1 gallons of DMF and the resulting solution cooled to about 20° C. 726 g. of 3-chloro-1-bromopropylbenzene were added in dropwise fashion. The reaction mixture was stirred at ambient temperature overnight and then poured onto ice. 3-Phenyl-3-(p-trifluoromethylphenoxy)propylchloride formed in the above reaction was extracted with hexane. The hexane extracts were separated and the hexane removed therefrom by evaporation in vacuo leaving an oily residue containing 3-phenyl-3-(p-trifluoromethylphenoxy)propylchloride plus a crystalline byproduct, 3-phenyl-3-(p-trifluoromethylphenoxy)propyl p-trifluoromethylphenylether. Distillation of an aliquot of this oily residue through a Vigreaux column yielded 3-phenyl-3-(p-trifluoromethylphenoxy)propylchloride boiling at about 115° C. at 0.07 torr.

Preferably however, the sodium salt of p-trifluoromethylphenol was prepared by taking 5.6 g. of a 50% NaH suspension in mineral oil and removing the mineral oil by washing with hexane under a nitrogen atmosphere. The washed NaH was added to 100 ml. of DMF. The mixture was cooled to about 5° C. A solution of 29.2 g. of 3-bromo-3-phenylpropylchloride and 20 g. of 3-p-trifluoromethylphenol in 75 ml. of DMF was added while maintaining the temperature below about 10° C. The reaction mixture was stirred at ambient temperature for 2.5 days. A small amount of ethanol was then added to decompose any residual NaH. The reaction mixture was then diluted with water to a volume of about 1.5 l. The aqueous mixture was extracted three times with hexane. The hexane extracts were combined and washed with 2 N aqueous sodium hydroxide, twice with water and finally with saturated aqueous sodium chloride. The hexane solution was dried and the solvent removed in vacuo leaving 39.25 g. of an oily residue consisting of 3-phenyl-3-(p-trifluoromethylphenoxy)propylchloride formed in the above reaction.

A solution of 83.5 g. of sodium azide in 250 ml. of water was placed in a 3 l., three-neck, round-bottom flask equipped with magnetic stirrer, condenser and thermometer. A solution of 100 g. of 3-phenyl-3-(p-trifluoromethylphenoxy)propylchloride in 750 ml. of DMF was added. The reaction mixture was heated to about 95° C. overnight and then cooled. Water was added and the aqueous layer extracted four times with equal volumes of ether. The ether extracts were combined, and the combined extracts washed five times with water and once with saturated aqueous sodium chloride. The solvents were removed by evaporation in vacuo to yield 91.5 g. of an oil. This oil was dissolved in 700 ml. of isopropanol and the resulting solution placed in a 2 l. round-bottom flask equipped with magnetic stirrer, condenser and drying tube. 28.4 g. of sodium borohydride were added thereto portionwise. After all the sodium borohydride had been added, the reaction mixture was heated to refluxing temperature overnight and was then cooled. The volatile constituents were evaporated in vacuo and the resulting residue taken up in water. The aqueous mixture was carefully acidified with 6 N aqueous hydrochloric acid. The aqueous mixture was then extracted three times with an equal volume of ether and the ether extracts discarded. The acidic layer was then made basic by the addition of 5 N aqueous sodium hydroxide. The alkaline mixture contained 3-phenyl-3-(p-trifluoromethylphenoxy)propylamine formed in the above reaction. This compound, being insoluble in base, separated, and was extracted into ether. The ether extraction was twice repeated. The ether extracts were combined and the combined extracts washed with saturated aqueous sodium chloride and then dried. Evaporation of the solvent yielded about 24.9 g. of 3-phenyl-3-(p-trifluoromethylphenoxy)propylamine.

24.9 g. of 3-phenyl-3-(p-trifluoromethylphenoxy)propylamine were dissolved in ethyl acetate. 7.55 g. of oxalic acid in ethyl acetate solution were added and the resulting mixture heated for about one hour. The oxalate salt precipitated and was collected by filtration. Recrystallization of the filter cake from an 80:20 ethyl acetate-methanol solvent mixture yielded 24.07 g. of 3-phenyl-3-(p-trifluoromethylphenoxy)propylamine oxalate melting at about 162°–164° C.

The hydrochloride salt was prepared in similar fashion and melted at about 135°–137° C.

The oxalate salt had the following analysis: Calc.: C, 56.11; H, 4.71; N, 3.63; F, 14.77. Found: C, 55.90; H, 4.41; N, 3.85; F, 14.52.

The hydrochloride salt had the following analysis: Calc.: C, 57.93; H, 5.17; N, 4.22; F, 17.18; Cl, 10.69. Found: C, 57.71; H, 5.05; N, 4.29; F, 16.98; Cl, 10.98.

EXAMPLE 4

Preparation of Salts

Salts of the free bases of this invention, other than the hydrochloride and oxalate salts whose preparation is illustrated above, are prepared by dissolving the free base in ether and adding an equivalent of a suitable non-toxic acid, also in ether. The salts thus formed, as for example the acetate and benzoate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include the sulfate, hydrobromide, phosphate, hydrogen phosphate, dihydrogen phosphate, acetate, methenesulfonate, succinate, tartrate, citrate, benzoate, and p-toluene sulfonate salts.

As indications of their psychotropic activity, the compounds of this invention have been found to block the uptake of various physiologically active monoamines. This blockade is shown both in vitro with radioactively labeled compounds to determine the amount of monoamine uptake by synaptosomes from rat brain, and in vivo by a variety of methods. Among the physiologically active monoamines whose uptake is blocked by the compounds of this invention are included serotonin, norepinephrine and dopamine (3,4-dihydroxyphenylethylamine). While all of the compounds of this invention block the uptake of monoamines, certain of them possess a unique selectivity in that they block the uptake of one of the monoamines to a far greater extent than they do the uptake of other monamines. Table 1 below sets forth the results of some of the in vitro determinations of the blockade of monoamine uptake by compounds of this invention. In the tables, column 1 give the R substituent (if any) on the 3-phenylpropylamine and columns 2-3, the concentration in micrograms per ml. that blocks the uptake of the particular amine by 50 percent of the amines—norepinephrine and serotonin. At the head of each column is given the concentration of the particular monoamine used in the experiment.

TABLE 1

$$R-O-\underset{\underset{C_6H_5}{|}}{CH}-CH_2-CH_2-NH_2$$

| R | Concentration in mcq./ml. that blocks 50% of amine uptake | |
|---|---|---|
|  | Norepinephrine 0.48 µM | Serotonin 0.1 µM |
| phenyl | .35 | 1.0 |
| p-trifluoromethylphenyl | 16 | 0.34 |

The tricyclic antidepressant drugs presently being marketed also inhibit the uptake of monoamines by brain neurons, most of them being more effective in inhibiting the uptake of norepinephrine than of serotonin. Many of the compounds of this invention behave similarly in that they block norepinephrine uptake more effectively than they do serotonin uptake. The p-trifluoromethyl derivative, however, is far more effective in inhibiting serotonin uptake than in inhibiting norepinephrine uptake. Thus, although the compounds of this invention clearly have potential as anti-depressant compounds, it is apparent that 3-(p-trifluoromethylphenoxy)-3-phenylpropylamine may have a different type of anti-depressant action from the presently marketed drugs, whether in its primary effect or in the severity and incidence of side effects. The compounds may also find use in the treatment of schizophrenia according to the hypothesis of Wyatt et al. Science, 177 1124 (1972). The authors were able to produce mild to moderate improvement in 6 of 7 chronic undifferentiated schizophrenic patients by the oral administration of 1-5-hydroxytryptophane, a serotonin precursor.

In addition to their usefulness as psychotropic agents, the above compounds may also find use in treating disorders of sleep, sexual performance, appetite, muscular function, and pituitary function. All of these physiologic functions have been shown to be subject to influence by brain serotoninergic neural systems.

In testing humans suffering from various psychoses having a depressive component, the compounds of this invention can be given orally or parenterally. In either instance, it is preferred to use an acid addition salt of the compound formed with a pharmaceutically-acceptable non-toxic acid. For purposes of oral administration, the salt can be mixed with standard pharmaceutical excipients and placed in telescoping gelatin capsules. Similarly, the salt can be mixed with starch, binders, etc. and formulated into tablets, which tablets may be scored for ease of divided dosage administration. For parenteral administration, a water soluble salt of a compound of this invention, which salt is pharmaceutically-acceptable, is dissolved in an isotonic solution and administered intramuscularly, intravenously or subcutaneously. For chronic administration, the oral pharmaceutical forms are naturally preferred. The dose level should vary from 1 to 50 mg./dose given from 1 to 4 times a day with a total daily dosage of 1 to 200 mg./day/human.

We claim:

1. 3-Phenyl-3-(p-trifluorophenoxy)propylamine, and its acid addition salts formed with pharmaceutically acceptable acids.

2. A compound accoding to claim 1, said compound being 3-phenyl-3-(p-trifluoromethylphenoxy)propylamine oxalate.

3. A compound according to claim 1, said compound being 3-phenyl-3-(p-trifluoromethylphenoxy)propylamine hydrochloride.

4. A compound accoding to claim 1, said compound being 3-phenyl-3-(p-trifluoromethylphenoxy)propylamine.

* * * * *